United States Patent
McConnell et al.

(12)

(10) Patent No.: US 6,235,924 B1
(45) Date of Patent: May 22, 2001

(54) CONTINUOUS PROCESS FOR PREPARING BENZOIC ACID ESTERS

(75) Inventors: Wesley Wayne McConnell; Bruce Edward Stanhope, both of Grayslake; Franz Josef Luxem, Palatine, all of IL (US)

(73) Assignee: Velsicol Chemical Corporation, Rosemont, IL (US)

( * ) Notice: Subject to any disclaimer, the term of this patent is extended or adjusted under 35 U.S.C. 154(b) by 0 days.

(21) Appl. No.: 09/633,712

(22) Filed: Aug. 7, 2000

(51) Int. Cl.⁷ .................................................. C07C 69/76
(52) U.S. Cl. .............................................................. 560/103
(58) Field of Search ............................................. 560/103

(56) References Cited

U.S. PATENT DOCUMENTS 5,302,746 * 4/1994 Koono et al. ........................ 560/205
5,446,190 * 8/1995 Billeb et al. ......................... 560/103

* cited by examiner

*Primary Examiner*—Joseph K. McKane
*Assistant Examiner*—Joseph Murray
(74) *Attorney, Agent, or Firm*—Robert Spector

(57) ABSTRACT

The present invention provides a continuous series of at least 3 esterification reactions, each of which yields highly pure esters derived from benzoic and at least one alcohol selected from monohydric alcohols containing from 6 to 12 carbon atoms and dihydric alcohols containing from 2 to 8 carbon atoms. At least a portion of the esterification catalyst and high boiling impurities remaining following distillation of the desired ester are used in the reaction mixture for the next reaction of the series.

14 Claims, No Drawings

CONTINUOUS PROCESS FOR PREPARING BENZOIC ACID ESTERS

BACKGROUND OF THE INVENTION

1. Field of the Invention

This invention relates to the preparation of benzoic acid esters. More particularly, this invention relates to a continuous batch process for preparing esters from mono- or dihydric alcohols and benzoic acid that may contain at least trace amounts of at least one of the three isomeric phthalic acids or phthalic anhydride. The resultant benzoic acid esters are at least 99 percent pure and substantially free of phthalic acid esters.

2. Description of the Prior Art

Methods for preparing esters, including those of aromatic acids such as benzoic and the three isomeric phthalic acids are well known. In accordance with one of these methods the carboxylic acid and the alcohol are typically reacted in the presence of a suitable catalyst. Because this type of esterification is usually an equilibrium reaction, to favor formation of the desired ester a stoichiometric excess of the alcohol reactant is typically used and the water formed as a by-product is continuously removed. Strong acids, stannates, and organic titanates are typical catalysts for esterification reactions.

If the boiling point of the final ester is sufficiently low, it can be isolated from the reaction mixture by distillation.

The distillation of esters prepared from 1) aromatic acids such as benzoic and phthalic acids and 2) alcohols containing less than 4 carbon atoms is known. For example, Japanese laid open application 60/94939, published on May 28, 1985 describes a method for purifying esters by treating the initial ester with a solid alkali or a concentrated alkaline solution followed by distillation of the resultant mixture. No conditions for the distillation are reported. The only esters exemplified are mono- and dimethyl phthalate.

Fractional distillation of dimethyl terephthalate at a temperature of 185–7° C. under a pressure of 50 torr is described by P.Zernov et al in Khim. Volokna (1975) (4) 27-8.

Distillation of ethyl 2,3,4,5-tetrafluorobenzoate is described in Japanese laid open application 11/130,734, laid open on May 18, 1999. The ester is prepared from the corresponding acid and alcohol in the presence of a sulfonic acid catalyst, which is subsequently recycled.

Steam distillation of esters prepared by reacting phthalic acid and an alcohol containing from 5 to 12 carbon atoms is described in Russian patent No. 763,322, published on Sep. 15, 1980. Steam distillation yields a mixture of the desired ester together with water, which must be removed as part of the purification procedure. Because removal of the last traces of water from an organic compound is difficult, expensive and time consuming, steam distillation is less than satisfactory when the objective is isolation of a high purity, substantially anhydrous ester directly from a reaction mixture.

The failure of the prior art to teach distillation of esters derived from aromatic acids and alcohols containing more than about 6 carbon atoms in the absence of steam suggests that conventional distillation of these esters is not feasible, particularly on a commercial scale, even under reduced pressures.

Commercially available grades of benzoic acid typically contains at least trace amounts of at least one of the three isomeric phthalic acids and/or phthalic anhydride. One source for these impurities is the presence of one or more of the three isomeric xylenes in the toluene that is oxidized in accordance with one of the more commonly used commercial processes for preparing benzoic acid. Zone refining and distillation have been used to separate benzoic acid from these impurities, however these methods are not cost efficient.

The toxicity to humans of esters derived from phthalic acid and alcohols containing 8 carbon atoms has been investigated by government regulatory agencies. Use of these esters as plasticizers in toys for children under 3 is banned in several European countries.

In the United States, for certain end use applications of the corresponding benzoic acid esters, for example as plasticizers for vinyl polymers such as polyvinyl chloride used as food grade packaging materials, the esters must contain no more than 0.1 percent by weight of the corresponding phthalic acid esters in order to avoid the reporting requirements of federal and state regulatory agencies.

One objective of this invention is to provide a semicontinuous process for preparing substantially pure esters from benzoic acid and either monohydric alcohols containing from 6 to 12 carbon atoms or dihydric alcohols containing from 2 to 8 carbon atoms.

SUMMARY OF THE INVENTION

This invention provides a method for preparing esters derived from at least one alcohol and benzoic acid, said method comprising conducting a first reaction, at least one intermediate reaction, and a final reaction, wherein the method for conducting said first reaction comprises:
  forming a first reaction mixture comprising
    (1) a mixture of carboxylic acids consisting essentially of benzoic acid and at least trace amounts of at least one compound selected from the group consisting of the three isomeric phthalic acids and phthalic anhydride; and
    (2) at least one alcohol selected from the group consisting of monohydric alcohols containing from 6 to 12 carbon atoms and dihydric alcohols containing from 2 to 8 carbon atoms, wherein the total number of moles of alcohol-bonded hydroxyl groups is equivalent to at least 1.02 times the number of moles of all carboxylic acids and carboxylic acid anhydrides present in said first reaction mixture;
  heating said first reaction mixture at the boiling point sufficiently to remove substantially all of the water generated as a by-product of the resultant reaction while maintaining a stoichiometric excess of said alcohol in said reaction mixture, and continuing said heating until substantially all of the carboxylic acids in said reaction mixture have reacted;
  distilling from said first reaction mixture under subatmospheric pressure substantially all unreacted alcohol and reaction products exhibiting a lower boiling point than said esters;
  distilling from said first reaction mixture under subatmospheric pressure substantially all benzoic acid esters and substantially none of any phthalic acid esters to form a first reaction residue;
the method for conducting said intermediate reaction comprises:
  forming an intermediate reaction mixture comprising
    (1) a mixture of carboxylic acids consisting essentially of benzoic acid and at least trace amounts of at least one compound selected from the group consisting of the three isomeric phthalic acids and phthalic anhydride;

(2) at least one alcohol selected from the group consisting of monohydric alcohols containing from 6 to 12 carbon atoms and dihydric alcohols containing from 2 to 8 carbon atoms, wherein the total number of moles of all alcohol-bonded hydroxyl groups is equivalent to at least 1.02 times the number of moles of all carboxylic acids and carboxylic acid anhydrides present in said intermediate reaction mixture;

(3) at least a portion of a residue selected from the group consisting of said first reaction residue and the residue from a preceding intermediate reaction;

heating said intermediate reaction mixture sufficiently to remove substantially all of the water generated as a by-product of the resultant reaction while maintaining a stoichiometric excess of said alcohol in said intermediate reaction mixture, and continuing said heating until substantially all of the carboxylic acids in said intermediate reaction mixture have reacted;

distilling from said intermediate reaction mixture under subatmospheric pressure substantially all unreacted alcohol and reaction products exhibiting a lower boiling point than said esters;

distilling from said intermediate reaction mixture under subatmospheric pressure substantially all benzoic acid esters and substantially none of any phthalic acid esters to form an intermediate reaction residue; and the method for conducting said final reaction comprises forming a final reaction mixture comprising (1) a mixture of carboxylic acids consisting essentially of benzoic acid and at least trace amounts of at least one compound selected from the group consisting of the three isomeric phthalic acids and phthalic anhydride;

(2) at least one alcohol selected from the group consisting of monohydric alcohols containing from 6 to 12 carbon atoms and dihydric alcohols containing from 2 to 8 carbon atoms, wherein the total number of moles of all alcohol-bonded hydroxyl groups is equivalent to at least 1.02 times the number of moles of all carboxylic acids and carboxylic acid anhydrides present in said third reaction mixture; and (3) at least a portion of said intermediate reaction residue;

heating said final reaction mixture sufficiently to remove substantially all of the water generated as a by-product of the resultant reaction while maintaining a stoichiometric excess of said alcohol in said final reaction mixture, and continuing said heating until substantially all of the carboxylic acids in said final reaction mixture have reacted;

distilling from said final reaction mixture under subatmospheric pressure substantially all unreacted alcohol and reaction products exhibiting a lower boiling point than said esters; and distilling from said final reaction mixture under subatmospheric pressure substantially all benzoic acid esters and substantially none of any phthalic acid esters.

In a preferred embodiment of the present method 1) a conventional esterification catalyst is added to the initial reaction mixture for only the first reaction of a series, and 2) at least a portion of any alcohol that is distilled together with the water formed as a by-product of the esterification reaction is returned to the reactor. Conventional esterification catalysts include but are not limited to mineral acids, organic sulfonic acids, stannates, and organic titanates.

DETAILED DESCRIPTION OF THE INVENTION

The method of the present invention is characterized by the ability to conduct a series of at least three esterification reactions in the same reactor without additional catalyst or the removal from the reactor of by-products formed during preceding reactions that exhibit a higher boiling point than the desired ester. These higher boiling by-products include but are not limited to esters derived from 1) one or more of the isomeric phthalic acids or phthalic anhydride, and 2) the alcohol(s) used in the present method.

Distillation of the final ester, which has not been taught in the prior art for benzoic acid esters of alcohols containing more than about 2 carbon atoms, reduces the concentration of phthalic acid esters in the desired benzoic acid ester to less than 1 percent, preferably less than 0.1 percent, determined using gas liquid chromatography.

The series of reactions conducted in accordance with the present method comprises a first reaction, at least one intermediate reaction and a final reaction. The following procedure is used for the first reaction of a series.

The First Esterification Reaction of a Series

1) Combining of Reactants and Optional Catalyst

The first step of the first reaction of a series comprises charging a reactor with benzoic acid and a stoichiometric excess, based on the number of moles of acid, of at least one monohydric alcohol containing from 6 to 12 carbon atoms and/or at least one dihydric alcohol containing from 2 to 8 carbon atoms. If an esterification catalyst is used, it is also added at this time.

Depending upon the method used to prepare it, commercially available grades of benzoic acid, with the exception of the U.S.P. grade, typically contains up to 0.4 weight percent of one or more of the three isomeric phthalic acids and/or phthalic anhydride.

Suitable monohydric alcohols for use in the method of the present invention include but are not limited to the isomeric hexanols, octanols, decanols and dodecanols. 2-ethylhexanol is a preferred monohydric alcohol, based on its cost and availability.

Suitable dihydric alcohols for use in the method of the present invention, based on their cost and availability, include but are not limited to ethylene glycol, propylene glycol, 1,4-butanediol and 1,6-hexanediol.

The molar ratio of the hydroxyl groups in all of the alcohols present in the reaction mixture to total carboxylic acids and acid anhydrides in the reaction mixtures of the present invention is greater than 1:1, typically from 1.02:1 up to about 2:1 or higher. Ratios of from 1.02:1 to 1.25:1 are preferred.

When an esterification catalyst is included in the reaction mixture, suitable catalysts include but are not limited to alkyl titanates and organic sulfonic acids such as p-toluenesulfonic acid. The acids can be immobilized on a suitable base such as a finely divided polystyrene.

Preferred catalysts are alkyl titanates wherein the alkyl groups contain from 2 to 8 carbon atoms. Tetraisobutyl titanate is a particularly preferred catalyst. The advantage of titanium compounds is their stability, which allows the catalyst to be recycled and used in up to 4 or more successive reactions with no significant loss of catalytic activity, and their high boiling point, which ensures that the catalyst will not distill together with the desired ester.

The concentration of catalyst is typically from 0.01 to 1.0 weight percent, based on the weight of benzoic acid added to the reactor. A preferred concentration range is from 0.01 to 0.1 weight percent.

2) Heating of Reactants and Catalyst

The reaction between benzoic acid and the alcohol(s) is conducted in a reactor equipped with means for heating the contents at least to the boiling point, under atmospheric pressure, of the alcohol used as one of the reactants. Preferably the reactor is equipped with means for condensing and storing the vaporized liquids evolved during the initial phase of the present method, and returning a portion of the condensed liquid to the reactor.

When the reaction mixture reaches its boiling point, the resultant vapor typically initially comprises at least the water formed as a by-product of the reaction. Esterification is typically a reversible equilibrium reaction yielding water and the desired ester as products. In accordance with the law governing equilibrium reactions, removal of the water from the reaction mixture will increase the relative concentration of the desired ester in the reaction mixture.

If the alcohol used as a reactant forms an azeotrope with water, the initial vapor comprises a mixture of water and the alcohol in the proportion defined by the law governing azeotropic mixtures. One of the preferred alcohols, 2-ethylhexanol, forms an azeotropic mixture with water that boils at a temperature of about 99° C. under atmospheric pressure.

If the alcohol reactant does not form an azeotropic mixture with water, a non-reactive organic liquid such as toluene that forms an azeotropic mixture with water can be included in the initial reaction mixture.

As the reaction proceeds and most of the by-product water is removed from the reaction mixture, the boiling point of the reaction mixture typically increases. The water content of the distillate typically decreases while the concentration of the alcohol(s) increases.

The course of the esterification reaction can be followed by measuring the volume of water collected and comparing this with the theoretical volume expected based on the weight of benzoic and any other carboxylic acids initially present in the reactor.

When substantially no additional water is collected as a distillate, which typically requires from 1 to about 24 hours, depending upon the amount of benzoic acid reactant, catalyst, number of hydroxyl groups on the alcohol and reaction temperature, distillation of the unreacted alcohol from the reaction mixture is begun.

At this stage of the present method, the concentration of unreacted benzoic acid in the reaction mixture is typically from 0.01 to 2.5 weight percent of its initial value.

3) Removal of Unreacted Alcohol

Because the mono- and dihydric alcohols suitable for use as reactants in the present method boil above about 150° C. under atmospheric pressure, to avoid thermally induced decomposition of the desired ester, distillation of these alcohols from the reaction mixture is typically conducted under pressure of from about 1 to about 100 mm of mercury. Under these conditions the boiling points of the present alcohols are from 80 to about 210° C.

To minimize the amount of desired ester distilled from the reactor together with the unreacted alcohol, preferably only a portion of the vaporized liquid is collected. The ratio of volume of liquid collected to that returned to the reactor is referred to as the reflux ratio. The effect of this reflux ratio and the number of theoretical stages in the reflux condenser on the efficiency of this stage of the present method should be apparent to those skilled in the art. The reflux ratio is preferably from 1:1 to 1:5.

As the unreacted alcohol is distilled from the reactor and collected, the temperature of the reaction mixture increases toward the boiling point of the desired ester(s). Distillation of the alcohol is continued until the concentration of alcohol in the reaction mixture is typically less than about 1 percent by weight, preferably less than 500 parts by weight per million.

4) Distillation of the Desired Ester

When a major portion of the unreacted alcohol has been distilled from the reaction mixture, the vapor temperature will increase above the boiling point of the alcohol reactant toward the boiling point of the desired ester. Collection of the desired ester is begun when the vapor temperature reaches the boiling point of this ester. One of the preferred esters, 2-ethylhexyl benzoate, boils at 182° C. under a pressure of 25 mm. Hg.

The boiling points of benzoic acid esters prepared using the present method are typically from 50 to 300 degrees C. under pressures of from 1 to 100 mm. Hg.

As described for distillation of the unreacted alcohol, during distillation of the ester a portion of the vaporized liquid is preferably returned to the reactor. The reflux ratio is adjusted to optimize product purity and efficiency of the distillation process. Those skilled in the art will recognize that the optimum reflux ratio will depend upon a number of variables, including the type of condenser used and the number of theoretical plates.

There is no teaching in the prior art concerning the distillation in the absence of steam of esters derived from benzoic acid and alcohols containing from 6 to 12 carbon atoms.

Distillation of the ester is continued until the volume of liquid in the reactor is reduced to from 5 to about 10 percent of the initial volume present at the beginning of the esterification reaction. It will be understood by those skilled in the art that the minimum residue volume that will avoid contamination of the distillate with undesirable by-products is a function of several variables, including by-product yield, heat input and reflux ratio.

The by-products present in the residue from the distillation include but are not limited to esters of phthalic acid and products of the thermally induced decomposition of compounds present in the initial reaction mixture. Some of these undesired products may impart color to the residue. It will be understood by those skilled in the art that the quantity of impurities in the residue will increase during the series of esterification reactions that characterize the present method.

The Intermediate Esterification Reactions of a Series

When distillation of the desired ester formed in the first reaction of a series is complete, the residue remaining in the reactor is allowed to cool to a temperature below the boiling point of the lowest boiling reactant of the esterification reaction. The intermediate esterification reactions of the present method are conducted by combining at least a portion of this residue with the benzoic acid, desired alcohol (s) and optional catalyst as described hereinbefore as part of the procedure for the first step of the initial reaction.

The present inventors found that the concentration of impurities in the final benzoic acid ester produced during succeeding reactions is reduced when only a portion of the residue from a preceding reaction is combined with the reactants for the next reaction of a series. To maintain uniformity in the concentration of impurities present in benzoic acid esters produced in successive reactions of a series, the amount of residue withheld is sufficient to establish a steady state concentration of impurities in the benzoic acid ester. The concept of achieving a steady state concentration of impurities in a product and methods for achieving it are sufficiently well understood that a detailed discussion in the present specification is not required.

The unreacted alcohol recovered by distillation during a previous esterification reaction can be used as a portion of the alcohol for a subsequent reaction. This recovered alcohol may contain undesirable impurities. It will be understood that the concentration of these impurities will increase each time the alcohol is recycled. Preferably a portion, usually about 10 percent by volume, of the recovered alcohol is discarded and replaced with previously unused alcohol. This will achieve a steady state concentration of impurities in the recycled alcohol and increase the number of times the esterification reaction can be repeated using recycled alcohol. As discussed in the preceding section with relation to reaction residues, the amount of recovered alcohol withheld is sufficient to establish a steady state concentration of impurities in the benzoic acid ester produced during succeeding reactions of a series.

As described in the procedure for conducting the initial reaction, the reactor is equipped with means for condensing the water and unreacted alcohol distilled during the esterification reaction, and returning at least a portion of the recovered alcohol to the reactor.

The procedures for heating the reaction mixture during the esterification reaction, distilling substantially all of the unreacted alcohol from the reaction mixture at the completion of this reaction and distilling the desired ester from the reaction mixture are described in the preceding section of this specification relating to the initial reaction of a series.

The Final Reaction of a Series

The major difference between the procedure for conducting the final reaction of a series and the preceding intermediate reactions is the molar ratio of alcohol-bonded hydroxyl groups to total carboxylic acids. For the final reaction this ratio is typically lower than the ratio used in the previous reaction, and is preferably from 1.03 to 1.07.

During the final reaction of a series, difficulty may be experienced in reaching the desired concentration of unreacted benzoic acid during the esterification reaction. This acid concentration is typically less than 1.5 weight percent. If this difficulty occurs, addition to the reactor of an additional amount of the alcohol reactant in an amount equivalent to about 2.5 mole percent of the alcohol originally present in the reactor typically helps to lower the acid concentration to the desired value.

The procedures for the addition of reactants to the reactor, conducting the reaction between the acid(s) and alcohol, and the distillations of unreacted alcohol and the desired ester during the final reaction of a series are substantially identical to those procedures described hereinbefore in the section relating to the intermediate reactions of the series.

A series of at least one initial, one intermediate and one final esterification reaction can be conducted using the present method. The number of intermediate esterification reactions conducted in a given series without any substantial decrease in product yield will be determined by the desired purity of the final ester, and the type of equipment used to conduct the reactions and distillations. Typically the intermediate esterification reactions are continued until it is no longer possible to achieve the desired degree of purity of the final ester.

It will be apparent to those skilled in the art that the number of cycles yielding a product of a desired purity can be increased by removing a portion of the residue remaining in the reactor following distillation of the ester. As discussed hereinbefore, recovered unreacted alcohol can be used as a portion of the alcohol reactant for a subsequent esterification reaction. The quantities of reaction residue and alcohol removed are sufficient to establish a desired steady state concentration of impurities in the esterification reaction mixture.

EXAMPLE

The following example demonstrates a preferred embodiment of the present process for preparing benzoic acid esters, and should not be interpreted as limiting the scope of the accompanying claims. Unless otherwise indicated, all parts and percentages are by weight.

The steps comprising each of the three or more esterification reaction that constitute the present method are 1) reaction of benzoic acid with 2-ethylhexanol; 2) removal of by-product water by distillation; 3) distillation of unreacted 2-ethylhexanol under reduced pressure and 4) distillation under reduced pressure of 2-ethylhexyl benzoate. The procedures for conducting these stages are described for the first reaction of a series, the intermediate reactions and the final reaction.

The Initial Reaction
Reaction of Benzoic acid and 2-Ethylhexanol

A glass reactor equipped with heating means, a fractionating column, reflux condenser and a trap for collecting distillate from the reflux condenser and returning the overflow to the reactor was charged with 760 parts of reagent grade benzoic acid containing less than 0.5 weight percent of the isomeric phthalic acid, 1015 parts of reagent grade 2-ethylhexanol and 0.45 parts of tetraisobutyl titanate as the esterification catalyst. The molar ratio of alcohol to acid was 1.25:1. The contents of the reactor were then heated with stirring at 250° C. A mixture of water and 2-ethylhexanol distilled and collected in the trap as two layers. The overflow from the trap (the upper portion of the 2-ethylhexanol layer) was allowed to return to the reactor. The water layer was periodically drained from the trap and discarded. Heating was continued for 3.1 hours, at which time the concentration of benzoic acid in the reactor was less than 0.2 weight percent. 114 parts of water were collected during the reaction.

Distillation of Unreacted 2-ethylhexanol

The contents of the reactor were then transferred to a distillation flask which was then connected to vacuum distillation apparatus. The apparatus included an Oldershaw type distillation column, a water-cooled reflux condenser, a nitrogen inlet and means to adjust the volume ratio of liquid distilled into a receiver to liquid returned to the distillation flask.

The unreacted 2-ethylhexanol was distilled from the reaction mixture by heating the contents of the distillation flask to boiling under a pressure of 25 mm mercury. The distillate was collected in a receiver using a reflux ratio of 1:1. When the vapor temperature reached 182° C. the first phase of the distillation was discontinued. 242.6 parts of distillate were collected, which contained 205 parts of 2-ethylhexanol.

Distillation of 2-ethylhexyl benzoate

With a new distillation receiver in place, heating of the material in the distillation flask was resumed under the same pressure of 25 mm. Hg. A distillation was conducted using a reflux ratio of 1:1. 1328 parts of a fraction exhibiting a vapor temperature of 182° C. was collected.

This distillate was analyzed using gas liquid chromatography. The results of this analysis are recorded in the following Table 2.

Following completion of the distillation 100.8 parts of residue remained in the distillation flask, and was used as a portion of the reaction mixture for the next reaction of the series.

The Intermediate Reactions

A series of three intermediate reactions were conducted using the following procedure.

Reaction of Benzoic Acid and 2-Ethylhexanol

The reactor was charged with the residue from the previous reaction of the series, an amount of distillate from the alcohol recovery step of the previous reaction containing 205 parts of 2-ethylhexanol, 760 parts of benzoic acid and 810 parts of unused 2-ethylhexanol. The contents of the reactor were heated at the boiling point, a mixture of water and 2-ethylhexanol distilled and the upper portion of the distilled 2-ethylhexanol layer returned to the reactor as described for the initial reaction. The heating times, amounts of water collected during each of the three reactions and the amount of unreacted benzoic acid remaining following the reactions are recorded in Table 1.

TABLE 1

|  | Reaction 1 | Reaction 2 | Reaction 3 |
| --- | --- | --- | --- |
| Heating Time (minutes) | 189 | 197 | 190 |
| Water Recovered (parts) | 113.0 | 112.2 | 112.4 |
| Unreacted Benzoic Acid (parts) | 2.88 | 3.30 | 3.42 |

Distillation of Unreacted 2-Ethylhexanol

The unreacted 2-ethylhexanol was distilled under reduced pressure as described for the initial reaction of the series. The amounts of this alcohol collected in each of the three intermediate reactions were 190.73 parts, 204.88 parts and 205.55 parts.

Distillation of 2-Ethylhexyl Benzoate

Following distillation of the 2-ethylhexanol the distillation receiver was replaced and 2-ethylhexyl benzoate distilled under reduced pressure as described for the initial reaction of the series. The three intermediate reactions yielded 1308.9, 1506.7 and 1476.5 parts by weight, respectively, of a distillate containing over 99.5 percent by weight of the desired ester. The distillates were analyzed using gas liquid chromatography and the results are recorded in the following Table 2.

The mixture remaining in the distillation flask from which the ester had been distilled was then allowed to cool, at which time it was combined with the reactants used in the next esterification reaction.

The Final Reaction

The reactor is charged with 82 parts of the residue from the previous reaction and an amount of recovered distillate from the previous reaction containing 205 parts of 2-ethylhexanol. 760 parts of benzoic acid and 810 parts of fresh 2-ethylhexanol were added to the reactor, at which time and the contents of the reactor were heated, a mixture of water and 2-ethylhexanol distilled and the 2-ethylhexanol returned to the reactor as described for the initial reaction. 113 parts of water were collected and the reaction mixture contained 4.68 parts of unreacted acid, indicating that 99.4 percent of the initial acid had reacted.

Distillation of Unreacted 2-Ethylhexanol

The unreacted 2-ethylhexanol was distilled under reduced pressure as described for the initial reaction of the series. 205 parts of this alcohol were collected Distillation of 2-Ethylhexyl Benzoate Following distillation of the 2-ethylhexanol the distillation receiver was replaced and 2-ethylhexyl benzoate distilled under reduced pressure as described for the initial reaction of the series. 1437 parts of a distillate containing 99.8 weight percent of the desired ester were collected. The distillate was analyzed using gas liquid chromatography (glc) and the results are recorded in the following Table 2.

The compounds present in the final distillates are represented in Table 2 by the following abbreviations:

2-EHA=2-ethylhexanol; BA=benzoic acid; 2-EIHB=2-ethylisohexyl benzoate;

2-EHB=2-ethylhexyl benzoate; DOP=dioctyl phthalate

TABLE 2

Analysis of 2-Ethylhexyl Benzoate

| | Percent of Total Peak Areas | | | | |
| --- | --- | --- | --- | --- | --- |
| | 2-EHA | BA | 2-EIHB | 2-EHB | DOP |
| Initial Reaction | 0.0236 | 0.0034 | 0.1916 | 99.77 | 0.0000 |
| Intermediate Reactions | | | | | |
| 1 | 0.0117 | 0.0000 | 0.1913 | 99.7643 | 0.0000 |
| 2 | 0.0125 | 0.0273 | 0.1989 | 99.7012 | 0.0000 |
| 3 | 0.0195 | 0.0059 | 0.2008 | 99.7100 | 0.0000 |
| Final Reaction | 0.0110 | 0.0050 | 0.1937 | 99.7580 | 0.0078 |

The data in Table 2 demonstrate that by distillation of the final ester the concentration of all impurities constitutes less than 1 percent by weight of the peak areas representing all products of the reaction.

That which is claimed is:

1. A method for preparing benzoic acid esters, said method comprising conducting a first reaction, at least one intermediate reaction, and a final reaction, wherein
    the method for conducting said first reaction comprises:
        forming a first reaction mixture comprising
            (1) a mixture of carboxylic acids consisting essentially of benzoic acid and at least trace amounts of at least one compound selected from the group consisting of the three isomeric phthalic acids and phthalic anhydride; and
            (2) at least one alcohol selected from the group consisting of monohydric alcohols containing from 6 to 12 carbon atoms and dihydric alcohols containing from 2 to 8 carbon atoms, wherein the total number of moles of alcohol-bonded hydroxyl groups is equivalent to at least 1.02 times the number of moles of all carboxyl groups and carboxylic acid anhydrides present in said first reaction mixture;
        heating said first reaction mixture at the boiling point sufficiently to remove substantially all of the water generated as a by-product of the resultant reaction while maintaining a stoichiometric excess of said alcohol in said reaction mixture, and continuing said heating until substantially all of the carboxylic acids in said reaction mixture have reacted;

distilling from said first reaction mixture under subatmospheric pressure substantially all unreacted alcohol and reaction products exhibiting a lower boiling point than said esters;

distilling from said first reaction mixture under subatmospheric pressure substantially all benzoic acid esters and substantially none of any phthalic acid esters to form a first reaction residue;

the method for conducting said intermediate reaction comprises:

forming an intermediate reaction mixture comprising
- (1) a mixture of carboxylic acids consisting essentially of benzoic acid and at least trace amounts of at least one compound selected from the group consisting of the three isomeric phthalic acids and phthalic anhydride;
- (2) at least one alcohol selected from the group consisting of monohydric alcohols containing from 6 to 12 carbon atoms and dihydric alcohols containing from 2 to 8 carbon atoms, wherein the total number of moles of alcohol-bonded hydroxyl groups is equivalent to at least 1.02 times the number of moles of all carboxyl groups and carboxylic acid anhydrides present in said intermediate reaction mixture;
- (3) at least a portion of a residue selected from the group consisting of said first reaction residue and the residue from a preceding intermediate reaction;

heating said intermediate reaction mixture sufficiently to remove substantially all of the water generated as a by-product of the resultant reaction while maintaining a stoichiometric excess of said alcohol in said intermediate reaction mixture, and continuing said heating until substantially all of the carboxylic acids in said intermediate reaction mixture have reacted;

distilling from said intermediate reaction mixture under subatmospheric pressure substantially all unreacted alcohol and reaction products exhibiting a lower boiling point than said esters;

distilling from said intermediate reaction mixture under subatmospheric pressure substantially all benzoic acid esters and substantially none of any phthalic acid esters to form an intermediate reaction residue; and the method for conducting said final reaction comprises
forming a final reaction mixture comprising
- (1) a mixture of carboxylic acids consisting essentially of benzoic acid and at least trace amounts of at least one compound selected from the group consisting of the three isomeric phthalic acids and phthalic anhydride;
- (2) at least one alcohol selected from the group consisting of monohydric alcohols containing from 6 to 12 carbon atoms and dihydric alcohols containing from 2 to 8 carbon atoms, wherein the total number of moles of alcohol-bonded hydroxyl groups is equivalent to at least 1.02 times the number of moles of all carboxyl groups and carboxylic acid anhydrides present in said third reaction mixture; and
- (3) at least a portion of said intermediate reaction residue;

heating said final reaction mixture sufficiently to remove substantially all of the water generated as a by-product of the resultant reaction while maintaining a stoichiometric excess of said alcohol in said final reaction mixture, and continuing said heating until substantially all of the carboxylic acids in said final reaction mixture have reacted;

distilling from said final reaction mixture under subatmospheric pressure substantially all unreacted alcohol and reaction products exhibiting a lower boiling point than said esters; and distilling from said final reaction mixture under subatmospheric pressure substantially all benzoic acid esters and substantially none of any phthalic acid esters.

2. A method according to claim 1 wherein a catalyst is added together with said acid mixture and said alcohol used in said first reaction.

3. A method according to claim 2 where said catalyst is an organic titanate and is present at a concentration of from 0.01 to 0.1 weight percent, based on the weight of benzoic acid.

4. A method according to claim 1 wherein said intermediate reaction is repeated at least 3 times.

5. A method according to claim 2 wherein the molar ratio of said alcohol-bonded hydroxyl groups to the total acids present in said mixture is from 1.2 to 1.4 in said first and intermediate reactions and from 1.03:1 to 1.07:1 in said final reaction; the contents of said reactor are heated at between 200 and 300 degrees C. during the reaction of said acids with said alcohol; said reaction is continued until the concentration of unreacted acids is less than 0.5 weight percent, based on the contents of said reactor; and said ester is distilled from said reactor under a pressure of less that 50 mm of mercury.

6. A method according to claim 1 where said alcohol contains 8 carbon atoms.

7. A method according to claim 6 where said alcohol is 2-ethylhexanol.

8. A method according to claim 1 wherein at least a portion of the alcohol used as the reactant in an intermediate or final reaction comprises at least a portion of the unreacted alcohol recovered by distillation during a previous reaction.

9. A method according to claim 8 wherein a portion of said alcohol is discarded.

10. A method according to claim 9 wherein the quantity of said alcohol discarded is sufficient to establish a steady state concentration of impurities among the benzoic acid esters produced during successive intermediate and final reaction mixtures.

11. A method according to claim 1 wherein a portion of a residue from a preceding reaction constitutes a portion of the reaction mixture for a succeeding intermediate or final reaction.

12. A method according to claim 11 wherein the quantity of said residue portion is sufficient to establish a steady state concentration of impurities among the benzoic acid esters produced during succeeding reactions.

13. A method according to claim 1 wherein the concentration of phthalic acid esters in said benzoic acid ester is less than 1 percent, as determined using gas liquid chromatography.

14. A method according to claim 13 wherein the concentration of said phthalic acid esters is less than 0.1 percent.

* * * * *